(12) United States Patent
Xiong et al.

(10) Patent No.: US 11,227,416 B2
(45) Date of Patent: Jan. 18, 2022

(54) IMAGE RECONSTRUCTION METHOD, APPARATUS, AND SYSTEM IN MAGNETIC RESONANCE IMAGING, AND STORAGE MEDIUM

(71) Applicant: Siemens Healthcare GmbH, Erlangen (DE)

(72) Inventors: Jun Xiong, Shenzhen (CN); Yan Tu Huang, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 112 days.

(21) Appl. No.: 16/695,229

(22) Filed: Nov. 26, 2019

(65) Prior Publication Data

US 2020/0167973 A1    May 28, 2020

(30) Foreign Application Priority Data

Nov. 28, 2018   (CN) .......................... 201811433623.2

(51) Int. Cl.
| | | |
|---|---|---|
| *G06K 9/00* | (2006.01) | |
| *G06T 11/00* | (2006.01) | |
| *G16H 30/40* | (2018.01) | |
| *G16H 40/67* | (2018.01) | |

(52) U.S. Cl.
CPC .......... *G06T 11/003* (2013.01); *G16H 30/40* (2018.01); *G16H 40/67* (2018.01); *G06T 2210/41* (2013.01)

(58) Field of Classification Search
CPC ... G06T 11/003; G06T 2210/41; G16H 30/40; G16H 40/67; A61B 5/0033; A61B 5/055
See application file for complete search history.

(56) References Cited

U.S. PATENT DOCUMENTS

| | | | | |
|---|---|---|---|---|
| 2015/0154747 A1* | 6/2015 | Mareachen | ........... | G06T 11/005 382/131 |
| 2015/0309150 A1* | 10/2015 | Zhang | ................ | G01R 33/5611 324/309 |
| 2019/0087986 A1* | 3/2019 | Spohn | .................... | G06T 11/006 |
| 2019/0286481 A1* | 9/2019 | Gatayama | .............. | G16H 30/40 |
| 2021/0158583 A1* | 5/2021 | Huang | ................ | G01R 33/561 |

FOREIGN PATENT DOCUMENTS

CN        107221014    *  9/2017  ............... A61B 6/52

* cited by examiner

*Primary Examiner* — Amara Abdi
(74) *Attorney, Agent, or Firm* — Schiff Hardin LLP

(57) ABSTRACT

The present disclosure is directed to image reconstruction techniques used in magnetic resonance imaging. The techniques disclosed include calculating, for each of image reconstruction tasks to be performed, a calculation capability requirement value of the task by a magnetic resonance system, and determining whether the calculation capability requirement value of the task is greater than a predetermined threshold. If so, the task is sent to a shared image reconstruction apparatus, so that the shared image reconstruction apparatus performs the task. Otherwise, the task is sent to a local image reconstruction apparatus, so that the local image reconstruction apparatus performs the task. The techniques described herein facilitate a reduction in hardware cost required for image reconstruction in MRI.

19 Claims, 7 Drawing Sheets

IMAGE RECONSTRUCTION METHOD, APPARATUS, AND SYSTEM IN MAGNETIC RESONANCE IMAGING, AND STORAGE MEDIUM

CROSS-REFERENCE TO RELATED APPLICATIONS

The present application claims the benefit of the filing date of China patent application no. 201811433623.2, filed on Nov. 28, 2018, the contents of which are incorporated herein by reference in their entirety.

TECHNICAL FIELD

The present disclosure relates to the field of Magnetic Resonance Imaging (MRI) technologies and, in particular, to an image reconstruction method, apparatus, a system in MRI, and a storage medium.

BACKGROUND

MRI technologies have become very useful in medical diagnoses. An MRI hardware system mainly comprises a magnet subsystem, a magnetic gradient (gradient for short) subsystem, a radio frequency subsystem, a spectrometer subsystem, and a master computer. The radio frequency subsystem mainly comprises a transmitting coil and a receiving coil; and the spectrometer subsystem mainly comprises a pulse sequence generator, a gradient waveform generator, a transmitter, a receiver, etc.

During the imaging process, and under the control of the pulse sequence generator, the transmitter outputs a radio frequency pulse signal to the radio frequency transmitting coil to generate a radio frequency field for exciting a hydrogen nucleus in a sample. After excitation by a radio frequency pulse, the hydrogen nucleus in the sample sends a Magnetic Resonance (MR) signal, this MR signal is received by the receiving coil placed near the sample, collected inside the receiver, and stored in the form of K-Space (space) data. Meanwhile, the K-Space data is sent to an image reconstruction apparatus, so that the image reconstruction apparatus reconstructs the K-Space data to obtain an image, and performs functions such as segmentation, identification, and other post-processing on the image.

With the development of magnetic resonance technologies, to improve the quality of a reconstructed image the receiving coil may concurrently collect MR signals in a multichannel manner. In addition, when collecting MR signals, the receiver may use sampling methods or techniques such as compressed sensing or blade. These two techniques enable the K-Space data to grow exponentially, thus imposing higher requirements on calculation resources of the image reconstruction apparatus. As a result, the image reconstruction apparatus requires a powerful CPU or GPU to provide sufficient calculation capabilities to obtain a magnetic resonance image and extract related information within a short enough time. However, the powerful calculation performance of the CPU and the GPU results in higher costs.

Moreover, the powerful computing performance of current systems is typically not fully used. For example, in one 3-hour scanning process of a volunteer, the actual usage condition of the CPU in a magnetic resonance image reconstruction machine generally operates such that time slices during which the usage rate of the CPU is below 5% occupy 98% of the entire scanning time period. This means that such expensive and high-performance hardware is only used in less than 2% of the time. In fact, when several systems are operated together in this manner, the idleness of hardware resources is more obvious.

SUMMARY

In order to solve the above-mentioned problem, the present disclosure provides an image reconstruction method in MRI to reduce the hardware costs required for image reconstruction in MRI.

To do so, the present disclosure provides an image reconstruction apparatus in MRI, an image reconstruction system in MRI, and a computer storage medium, each being directed to reducing the cost expended for image reconstruction in MRI.

In order to achieve the above-mentioned objectives, the present disclosure provides the technical solutions as follows:

an image reconstruction method in magnetic resonance imaging is provided, the method comprising:
calculating, for each of image reconstruction tasks to be performed, a calculation capability requirement value of the task by a magnetic resonance (MR) system; and
determining whether the calculation capability requirement value of the task is greater than a predetermined threshold and, if so, sending the task to a shared image reconstruction apparatus so that the shared image reconstruction apparatus performs the task, and otherwise sending the task to a local image reconstruction apparatus so that the local image reconstruction apparatus performs the task, wherein the calculation performance (e.g. processing power) of the shared image reconstruction apparatus is higher than the calculation performance of the local image reconstruction apparatus, and the shared image reconstruction apparatus is shared among a plurality of MR systems.

Calculating the calculation capability requirement value of the task comprises: (i) performing a weighted calculation on the amount of data processed for the task and a calculation complexity of the task so as to obtain the calculation capability requirement value of the task; or (ii) performing a weighted calculation of a duration of time required to feedback a calculation result for the task (i.e. a calculated "feedback duration" as used herein), the amount of data processed for the task, and a calculation complexity of the task, so as to obtain the calculation capability requirement value of the task.

Before calculating the calculation capability requirement value of the task, the method further comprises:
determining, according to a predetermined grading standard for calculating the duration of time required to feedback a calculation result for the task, a grade corresponding to the calculated feedback duration for the task, wherein the shorter the calculated feedback duration, the higher the corresponding grade value;
determining, according to a predetermined grading standard for amount of data, a grade value corresponding to the amount of data processed for the task, wherein the greater the amount of data, the higher the corresponding grade value; and
determining, according to predetermined calculation complexities of different algorithms, calculation complexities of various algorithms used in the task, and summing the calculation complexities of the algorithms used in the task so as to obtain the calculation complexity of the task, wherein the more complex the algorithm, the higher the calculation complexity of the algorithm;

and wherein performing the weighted calculation on the calculated feedback duration for the task, the amount of data processed for the task, and the calculation complexity of the task comprises:

performing a weighted calculation on the grade value corresponding to the required calculated feedback duration for the task, the grade value corresponding to the amount of data processed for the task, and the calculation complexity of the task.

An image reconstruction method in magnetic resonance imaging is provided, the method comprising:

receiving, by a shared image reconstruction apparatus, an image reconstruction task sent by any of MR systems that share this apparatus, wherein the image reconstruction task is an image reconstruction task in image reconstruction tasks to be reconstructed generated by the magnetic resonance system that has a calculation capability requirement value greater than a predetermined threshold;

calculating the priority of the task;

placing the task into a task queue according to the priority of the task, wherein tasks in the task queue are arranged sequentially in descending order of priorities; and sequentially reading tasks from the task queue, and performing the read tasks.

Calculating the priority of the task comprises:
performing a weighted calculation on the calculation capability requirement value of the task and a waiting duration for the task in the task queue so as to obtain the priority of the task, wherein the calculation capability requirement value is calculated, based on a calculated duration of time required to feedback a calculation result for the task, the amount of data processed for the task and a calculation complexity of the task, and sent by the MR system to the shared image reconstruction apparatus; or performing a weighted calculation of the required feedback duration for the task, the amount of data processed for the task, a calculation complexity of the task, and a waiting duration for the task in the task queue, so as to obtain the priority of the task, wherein the calculated required feedback duration result for the task is sent by the MR system.

Before performing the weighted calculation on the required feedback duration for the task, the amount of data processed for the task, the calculation complexity of the task, and the waiting duration for the task in the task queue, the method further comprises:

determining, according to a predetermined grading standard for calculating the required feedback duration, a grade corresponding to the calculated feedback duration for the task, wherein the shorter the required feedback duration, the higher the corresponding grade value;

determining, according to a predetermined grading standard for amount of data, a grade value corresponding to the amount of data processed for the task, wherein the greater the amount of data, the higher the corresponding grade value;

determining, according to predetermined calculation complexities of different algorithms, calculation complexities of various algorithms used in the task, and summing the calculation complexities of the algorithms used in the task so as to obtain the calculation complexity of the task, wherein the more complex the algorithm, the higher the calculation complexity of the algorithm; and determining, according to a predetermined grading standard for waiting duration for a task in a task queue, a grade value corresponding to the waiting duration for the task in the task queue, wherein the longer the waiting duration for the task in the task queue, the higher the corresponding grade value.

Performing the weighted calculation on the calculated required feedback duration for the task, the amount of data processed for the task, the calculation complexity of the task, and the waiting duration for the task in the task queue comprises:

performing a weighted calculation on the grade value corresponding to the calculated required feedback duration for the task, the grade value corresponding to the amount of data processed for the task, the calculation complexity of the task, and the grade value corresponding to the waiting duration for the task in the task queue.

The method further comprises:
recalculating, when a task is newly added to the task queue or a task has been performed, the priority of each task, and adjusting the position of each task in the task queue based on a calculation result.

An image reconstruction apparatus in magnetic resonance imaging is provided, the apparatus being located in a magnetic resonance (MR) system, the apparatus comprising:

a calculation capability requirement value calculation module for calculating, for each of image reconstruction tasks to be performed, a calculation capability requirement value of the task; and a task distribution module for determining whether the calculation capability requirement value obtained, via calculation by the calculation capability requirement value calculation module is greater than a predetermined threshold, and if so, sending the image reconstruction task to be performed to a shared image reconstruction apparatus so that the shared image reconstruction apparatus performs the task, and otherwise sending the image reconstruction task to be performed to a local image reconstruction apparatus so that the local image reconstruction apparatus performs the task, wherein the calculation performance of the shared image reconstruction apparatus is higher than the calculation performance of the local image reconstruction apparatus, and the shared image reconstruction apparatus is shared among a plurality of MR systems.

Calculating the calculation capability requirement value of the task by the calculation capability requirement value calculation module comprises: (i) performing a weighted calculation on the amount of data processed for the task and a calculation complexity of the task so as to obtain the calculation capability requirement value of the task; or (ii) performing a weighted calculation on a calculated duration of time required to feedback a calculation result for the task, the amount of data processed for the task, and a calculation complexity of the task, so as to obtain the calculation capability requirement value of the task.

An image reconstruction apparatus in magnetic resonance imaging is provided, the apparatus being located in a shared image reconstruction apparatus, and the shared image reconstruction apparatus being shared among a plurality of MR systems, wherein the image reconstruction apparatus in magnetic resonance imaging comprises:

a task priority calculation module for receiving an image reconstruction task sent by an MR system, and calculating the priority of the task, wherein the image reconstruction task is an image reconstruction task in image reconstruction tasks to be reconstructed generated by the magnetic resonance system that has a calculation capability requirement value greater than a predetermined threshold;

a task queue management module for placing the image reconstruction task into a task queue according to the priority of the image reconstruction task obtained, by calculation, by the task priority calculation module, wherein tasks in the task queue are arranged sequentially in descending order of priorities; and a task performing module for sequentially reading tasks from the task queue, and performing the read tasks.

Calculating the priority of the task by the task priority calculation module comprises: (i) performing a weighted calculation on the calculation capability requirement value of the task and a waiting duration for the task in the task queue so as to obtain the priority of the task, wherein the calculation capability requirement value is calculated, based on a calculated duration of time required to feedback a calculation result for the task, the amount of data processed for the task, and a calculation complexity of the task, and sent by the MR system to the task priority calculation module; or (ii) performing a weighted calculation on a required calculated required feedback duration to perform the task, the amount of data processed for the task, a calculation complexity of the task, and a waiting duration for the task in the task queue, so as to obtain the priority of the task, wherein the calculated required feedback duration to perform the task is sent by the MR system.

The task queue management module further comprises: notifying, when a task is newly added to the task queue or a task has been performed, the task priority calculation module of recalculating the priority of each task, and adjusting the position of each task in the task queue based on a new priority of each task obtained, by calculation, by the task priority calculation module.

An image reconstruction system in magnetic resonance imaging is provided, the system comprising: a plurality of MR systems and one shared image reconstruction apparatus, wherein the MR system comprises the image reconstruction apparatus in magnetic resonance imaging as described above, and the shared image reconstruction apparatus comprises the image reconstruction apparatus in magnetic resonance imaging as described in any of the above.

A computer readable storage medium is provided, which has a computer program stored thereon, wherein when the computer program is executed by a processor, steps of the image reconstruction method in magnetic resonance imaging as described in any of the above are implemented.

An image reconstruction apparatus in magnetic resonance imaging is provided, the apparatus comprising: a processor and a memory,
wherein the memory stores an application program executable by the processor that is used to cause the processor to perform steps of the image reconstruction method in magnetic resonance imaging as described in any of the above.

The present disclosure involves calculating a calculation capability requirement value of an image reconstruction task, and sending a task with a higher calculation capability requirement to a shared image reconstruction apparatus with a higher calculation performance for performing the task, and otherwise sending the task to a local image reconstruction apparatus with an ordinary calculation performance such that a plurality of MR systems may share one image reconstruction apparatus with a higher property, and the hardware cost required for image reconstruction is reduced.

Preferred embodiments are described below with reference to the accompanying drawings in an explicit and comprehensible manner, and the above characteristics, technical features, advantages, and embodiments are further described.

BRIEF DESCRIPTION OF THE DRAWINGS/FIGURES

The following accompanying drawings merely illustratively, which describe and explain the present disclosure and are not intended to limit the scope of the present disclosure.

Figure 1:
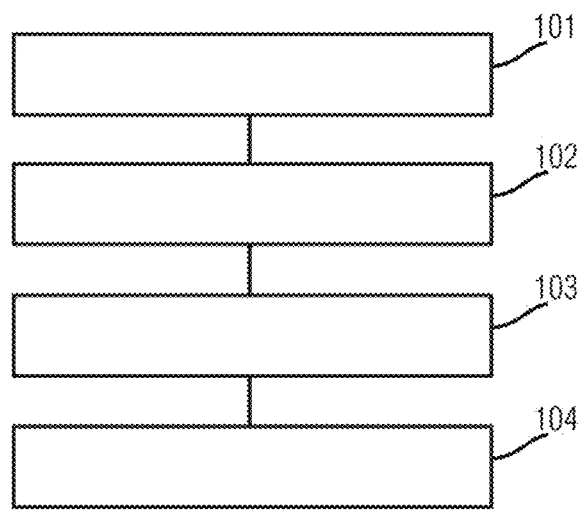
FIG. 1 is a flow chart of an image reconstruction method in MRI provided in an embodiment of the present disclosure.

Reference signs in the accompanying drawings are as follows:

| Reference numerals | Meaning |
|---|---|
| 101 to 104 | Step |
| 201 to 204 | Step |
| 301 to 309 | Step |
| 411 to 414 | MR system |
| 421 to 424 | Local image reconstruction apparatus |
| 43 | Switch |
| 44 | Shared image reconstruction apparatus |
| 50 | Image reconstruction apparatus in MRI provided in an embodiment of the present disclosure |
| 51 | Calculation capability requirement value calculation module |
| 52 | Task distribution module |
| 60 | Image reconstruction apparatus in MRI provided in another embodiment of the present disclosure |
| 61 | Task priority calculation module |
| 62 | Task queue management module |
| 63 | Task performing module |
| 70 | Image reconstruction apparatus in MRI provided in still another embodiment of the present disclosure |
| 71 | Processor |
| 72 | Memory |

DETAILED DESCRIPTION

In order to more clearly understand the technical features, objectives, and effects of the present disclosure, the specific embodiments of the present disclosure are described with reference to the accompanying drawings, and in the drawings, the same number represents components of the same structure or of similar structures but the same function.

The word "exemplary" represents "serving as an instance, example or description" herein, and any illustration and embodiment described as "exemplary" herein should not be interpreted as a more preferred or more advantageous technical solution.

Detailed Description of Embodiments

In order to make the objectives, technical solutions, and advantages of the present disclosure clearer, the technical solutions of the present disclosure are further described in detail below in conjunction with the accompanying drawings and based on the embodiments.

The terms "a/an" and "said" in the singular form used in the description of the present disclosure and the appended claims are also intended to include the plural form unless otherwise clearly specified in the context herein.

The present disclosure is now described in further detail below.

FIG. 1 is a flow chart of an image reconstruction method in MRI provided in an embodiment of the present disclosure, and the specific steps of the method are as follows:

Step 101: an MR system calculates, for each of image reconstruction tasks to be performed, a calculation capability requirement value of the task.

Step 102: the MR system determines whether the calculation capability requirement value of the task is greater than a predetermined threshold, and if so, performs step 103; otherwise, performs step 104.

The specific value of the predetermined threshold may be determined through a plurality of experiments.

Step 103: the MR system sends the task to a shared image reconstruction apparatus, so that the shared image reconstruction apparatus performs the task, and this procedure is ended.

Step 104: the MR system sends the task to a local image reconstruction apparatus, so that the local image reconstruction apparatus performs the task.

The calculation performance of the shared image reconstruction apparatus is higher than the calculation performance of the local image reconstruction apparatus, and the shared image reconstruction apparatus is shared among a plurality of MR systems.

Figure 2:
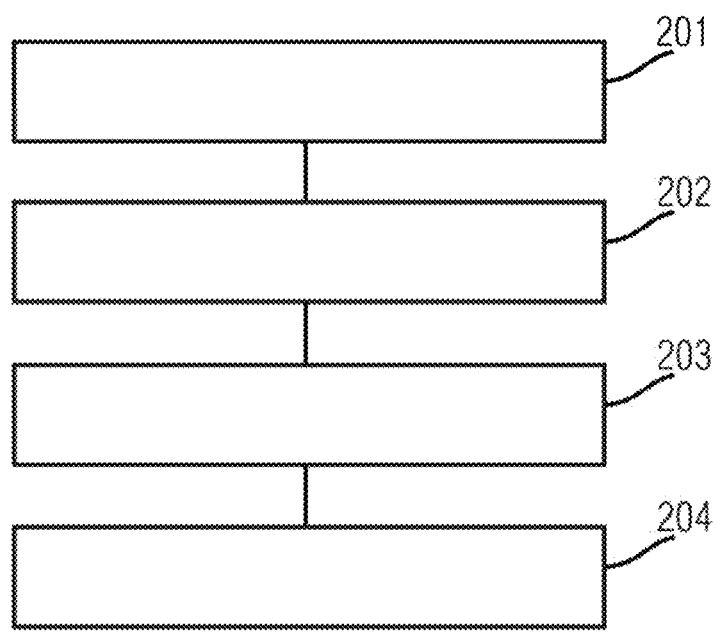
FIG. 2 is a flow chart of an image reconstruction method in MRI provided in another embodiment of the present disclosure.

FIG. 2 is a flow chart of an image reconstruction method in MRI provided in another embodiment of the present disclosure, and the specific steps of the method are as follows:

Step 201: a shared image reconstruction apparatus receives an image reconstruction task sent by any of MR systems that share this apparatus, wherein the image reconstruction task is an image reconstruction task in image reconstruction tasks to be reconstructed generated by the MR system that has a calculation capability requirement value greater than a predetermined threshold.

Step 202: the shared image reconstruction apparatus calculates the priority of the task.

In practical applications, the shared image reconstruction apparatus may calculate the priority of the task according to the following parameters:
I. the calculation capability requirement value of the task sent by the MR system;
II. the calculation capability requirement value of the task sent by the MR system and a waiting duration for the task in the task queue;
III. a calculated duration of time required to feedback a calculation result for the task, the amount of data processed for the task, and the calculation complexity of the task; and
IV. the calculated feedback duration for the task, the amount of data processed for the task, a calculation complexity of the task, and the waiting duration for the task in the task queue.

Step 203: the shared image reconstruction apparatus places the task into a task queue according to the priority of the task, wherein tasks in the task queue are arranged sequentially in descending order of priorities.

Step 204: the shared image reconstruction apparatus sequentially reads tasks from the task queue, and performs the read tasks.

Figure 3:
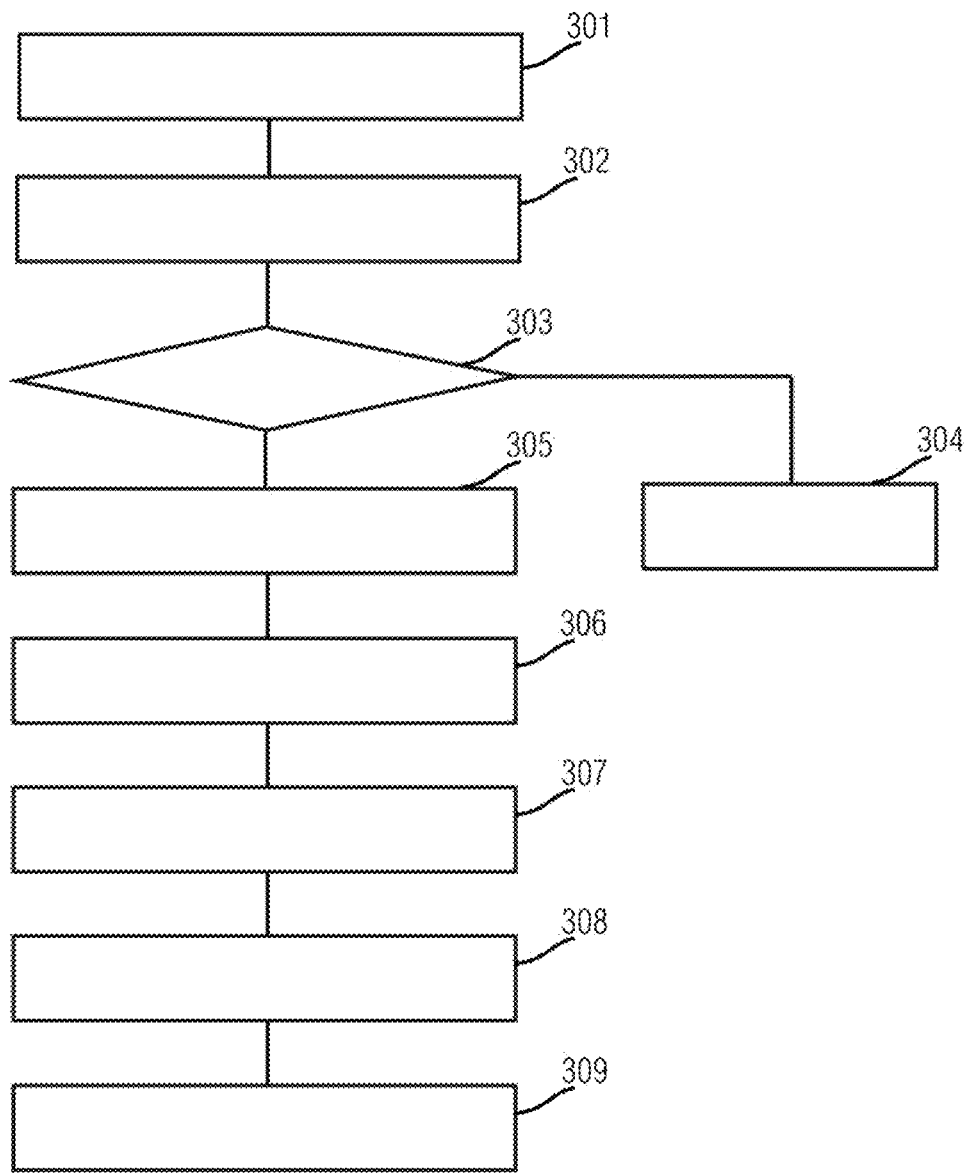
FIG. 3 is a flow chart of an image reconstruction method in MRI provided in still another embodiment of the present disclosure.

FIG. 3 is a flow chart of an image reconstruction method in MRI provided in still another embodiment of the present disclosure, and the specific steps of the method are as follows:

Step 301: an MR system has collected K-Space data, and creates an image reconstruction task.

The image reconstruction task comprises task content and K-Space data processed for the task, wherein the task content includes: one or more actions, one or more algorithms used by each action, etc.

Step 302: the MR system performs a weighted calculation on a calculated duration of time required to feedback a calculation result for the image reconstruction task, the amount of K-Space data processed for the task, and a calculation complexity of the task, so as to obtain the calculation capability requirement value of the task.

The calculated feedback duration required to perform the image reconstruction task is predetermined by a user.

In practical applications, the calculation capability requirement value of the image reconstruction task may be obtained by using the following steps:

Step 3021: determining, according to a predetermined grading standard for calculating required feedback durations, a grade corresponding to the calculated duration of time required to feedback a calculation result the task, wherein the shorter the calculated feedback duration, the higher the corresponding grade value.

For example, the total range of the calculated required feedback duration is divided into a plurality of intervals of equal lengths, and each of the intervals corresponds to one grade value, wherein the shorter the calculated feedback duration corresponding to one interval, the higher the grade value corresponding to the interval.

Step 3022: determining, according to a predetermined grading standard for amount of data, a grade value corresponding to the amount of data processed for the task, wherein the greater the amount of data, the higher the corresponding grade value.

For example, the total range of the amount of K-Space data is divided into a plurality of intervals of equal lengths, and each of the intervals corresponds to one grade value, wherein the greater the amount of data corresponding to one interval, the higher the grade value corresponding to the interval.

Step 3023: determining, according to predetermined calculation complexities of different algorithms, calculation complexities of various algorithms used in the task, and summing the calculation complexities of the algorithms used in the task so as to obtain the calculation complexity of the task, wherein the more complex the algorithm, the higher the calculation complexity of the algorithm.

Step 3024: performing a weighted calculation on the grade value corresponding to the calculated duration of time required to feedback a calculation result the task, the grade value corresponding to the amount of data processed for the task, and the calculation complexity of the task, so as to obtain the calculation capability requirement value of the task.

The weights of the calculated required feedback duration for the task, the amount of data processed for the task, and the calculation complexity of the task are predetermined, and the sum of the weights of the three is 1.

Step 303: the MR system determines whether the calculation capability requirement value of the task is greater than a predetermined threshold, and if so, performs step 305, otherwise, performs step 304.

Step 304: the MR system sends the task to a local image reconstruction apparatus for processing, and this procedure is ended.

Step 305: the MR system sends the task to a shared image reconstruction apparatus.

The MR system may send the calculation capability requirement value of the task and the task together to the shared image reconstruction apparatus; or the MR system may send the calculated duration of time required to feedback a calculation result for the task and the task together to the shared image reconstruction apparatus.

Step 306: the shared image reconstruction apparatus receives the task, and places the task into a local memory.

The local memory is, for example, a high-performance disk array.

Step 307: the shared image reconstruction apparatus performs a weighted calculation on the calculation capability requirement value of the task and the waiting duration for the task in the task queue, so as to obtain the priority of the task; or the shared image reconstruction apparatus performs a weighted calculation on the calculated duration of time required to feedback a calculation result for the task, the amount of data processed for the task, the calculation complexity of the task, and the waiting duration for the task in the task queue, so as to obtain the priority of the task.

If the MR system sends the calculation capability requirement value of the task to the shared image reconstruction apparatus, the shared image reconstruction apparatus performs a weighted calculation on the calculation capability requirement value of the task and the waiting duration for the task in the task queue, so as to obtain the priority of the task; or if the MR system does not send the calculation capability requirement value of the task to the shared image reconstruction apparatus, but sends only the calculated feedback duration required for the task, the shared image reconstruction apparatus performs a weighted calculation on the calculated duration of time required to feedback a calculation result for the task, the amount of data processed for the task, the calculation complexity of the task, and the waiting duration for the task in the task queue, so as to obtain the priority of the task.

Specifically, the following manner may be used by the shared image reconstruction apparatus to perform a weighted calculation on the calculated the duration of time required to feedback a calculation result for the task, the amount of data processed for the task, the calculation complexity of the task, and the waiting duration for the task in the task queue:

Step 3071: determining, according to a predetermined grading standard for calculating required feedback durations, a grade corresponding to the calculated duration of time required to feedback a calculation result for the task, wherein the shorter the calculated feedback duration required for the task, the higher the corresponding grade value.

For example, the total range of the calculated duration of time required to feedback a calculation result for the task is divided into a plurality of intervals of equal lengths, and each of the intervals corresponds to one grade value, wherein the shorter the calculated feedback duration required for the task corresponding to one interval, the higher the grade value corresponding to the interval.

For example, the total range of the required calculation of the duration of time required to feedback a calculation result for the task is divided into five intervals of equal lengths, and 1 to 5 are respectively used to represent the grade values corresponding to the intervals.

Step 3072: determining, according to a predetermined grading standard for amount of data, a grade value corresponding to the amount of data processed for the task, wherein the greater the amount of data, the higher the corresponding grade value.

For example, the total range of the amount of K-Space data is divided into a plurality of intervals of equal lengths, and each of the intervals corresponds to one grade value, wherein the greater the amount of data corresponding to one interval, the higher the grade value corresponding to the interval.

For example, the total range of the amount of K-Space data is divided into five intervals of equal lengths, and 1 to 5 are respectively used to represent the grade values corresponding to the intervals.

Step 3073: determining, according to predetermined calculation complexities of different algorithms, calculation complexities of various algorithms used in the task, and summing the calculation complexities of the algorithms used in the task, so as to obtain the calculation complexity of the task, wherein the more complex the algorithm, the higher the calculation complexity of the algorithm.

Step 3074: determining, according to a predetermined grading standard for waiting duration for a task in a task queue, a grade value corresponding to the waiting duration for the task in the task queue, wherein the longer the waiting duration for the task in the task queue, the higher the corresponding grade value.

For example, the total range of the waiting duration for the task in the task queue is divided into a plurality of intervals of equal lengths, and each of the intervals corresponds to one grade value, wherein the longer the waiting duration corresponding to one interval, the higher the grade value corresponding to the interval.

For example, the total range of the waiting duration for the task in the task queue is divided into five intervals of equal lengths, and 1 to 5 are respectively used to represent the grade values corresponding to the intervals.

When the task has not been placed into the task queue yet, the waiting duration for the task in the task queue is 0.

Step 3075: performing a weighted calculation on the grade value corresponding to the calculated duration of time required to feedback a calculation result for the task, the grade value corresponding to the amount of data processed for the task, the calculation complexity of the task, and the grade value corresponding to the waiting duration for the task in the task queue.

The weights of the grade value corresponding to the duration of time required to feedback a calculation result for the task, the grade value corresponding to the amount of data processed for the task, the calculation complexity of the task, and the grade value corresponding to the waiting duration for the task in the task queue are predetermined, and the sum of the weights of the four is 1.

Step 308: the shared image reconstruction apparatus inserts the task into a task queue according to the priority of the task, wherein tasks in the task queue are arranged in descending order of priorities, that is, the higher the priority of the task, the closer to the front the position, and the more likely the task is processed.

Step 309: the shared image reconstruction apparatus sequentially reads tasks from the task queue, reads the task content and K-Space data of the task from the local memory and loads the task content and K-Space data of the task into a memory to start calculation, and after the calculation is completed, returns obtained data of a reconstructed image and related results to the MR system that initiates the task.

When a new task is added to the task queue or a task has been performed in the task queue, the shared image reconstruction apparatus updates the priority of each task in the task queue according to a waiting duration for each task in the task queue, and adjusts the order of each task in the task queue based on a calculation result.

Because the waiting duration for the task in the task queue is taken into account during the calculation of the priority of the task, and the priority of each task is updated when a new task is added to the task queue or a task has been performed in the task queue, it is possible to avoid the case that a task with a lower priority is always arranged last and thus may never be processed.

The local image reconstruction apparatus and the shared image reconstruction apparatus in the embodiments of the present disclosure are distinguished in terms of calculation performance, and the calculation performance of the shared image reconstruction apparatus is higher than the calculation performance of the local image reconstruction apparatus. For example, the local image reconstruction apparatus may be a computer that uses an X86 or ARM platform, while the shared image reconstruction apparatus may be a server configured with a powerful CPU and GPU, and the shared image reconstruction apparatus may extend and upgrade configurations according to a supported MR system and the increase of the number of channels.

Figure 4:
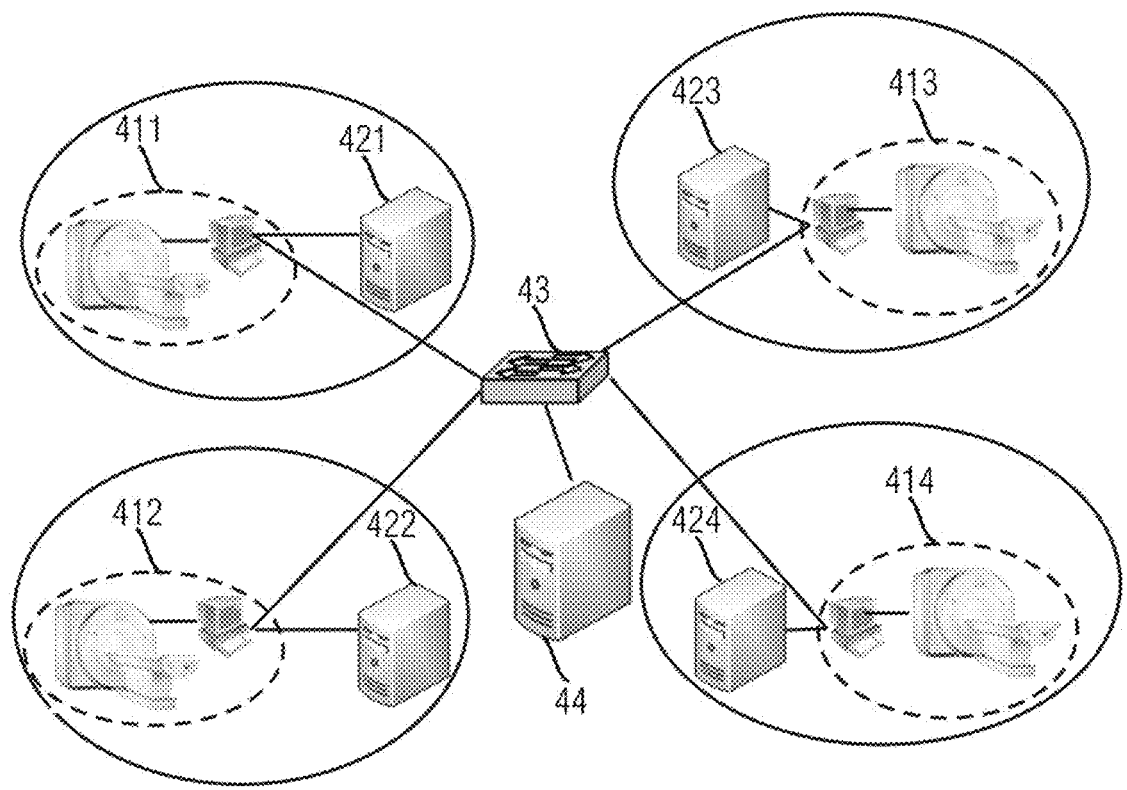
FIG. 4 is an architectural diagram of an image reconstruction system in MRI provided in an embodiment of the present disclosure.

FIG. 4 is an architectural diagram of an image reconstruction system in MRI provided in an embodiment of the present disclosure, wherein 411 to 414 are respectively MR systems, 421 to 424 are respectively local image reconstruction apparatuses of the MR systems, 43 is a switch, and 44 is a shared image reconstruction apparatus.

Figure 5:
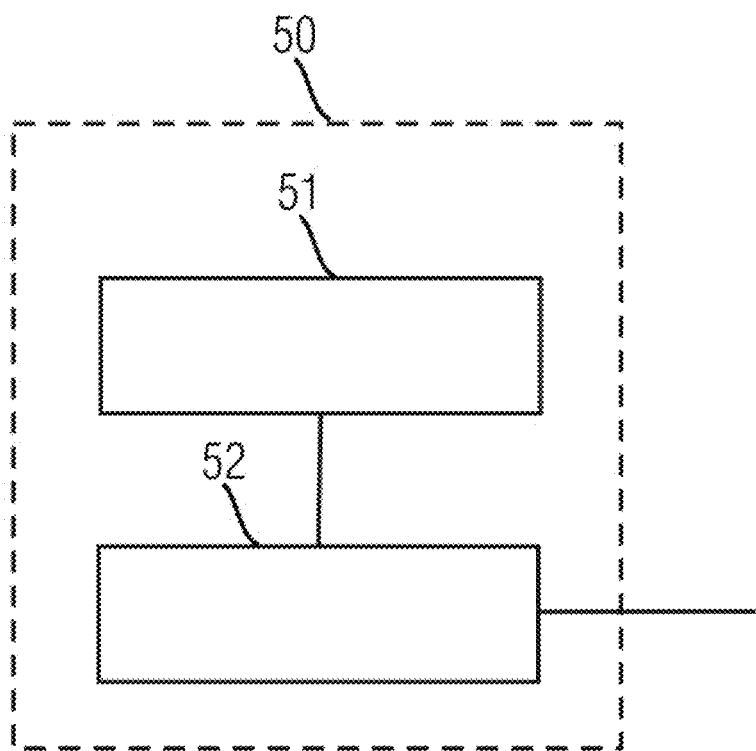
FIG. 5 is a schematic structural diagram of an image reconstruction apparatus in MRI provided in an embodiment of the present disclosure.

FIG. 5 is a schematic structural diagram of an image reconstruction apparatus 50 in MRI provided in an embodiment of the present disclosure. The apparatus is located in an MR system, and the apparatus 50 mainly comprises: a calculation capability requirement value calculation module 51 and a task distribution module 52.

The calculation capability requirement value calculation module 51 calculates, for each of image reconstruction tasks to be performed, a calculation capability requirement value of the task, and sends the task and the calculation capability requirement value of the task to the task distribution module 52.

The task distribution module 52 receives the image reconstruction task and the calculation capability requirement value of the task which are sent by the calculation capability requirement value calculation module 51, determines whether the calculation capability requirement value is greater than a predetermined threshold, and if so, sends the image reconstruction task to a shared image reconstruction apparatus, so that the shared image reconstruction apparatus performs the task, and otherwise sends the image reconstruction task to a local image reconstruction apparatus so that the local image reconstruction apparatus performs the task, wherein the calculation performance of the shared image reconstruction apparatus is higher than the calculation performance of the local image reconstruction apparatus, and the shared image reconstruction apparatus is shared among a plurality of MR systems.

In one optional embodiment, calculating the calculation capability requirement value of the task by the calculation capability requirement value calculation module 51 comprises:
performing a weighted calculation on the amount of data processed for the task and a calculation complexity of the task, so as to obtain the calculation capability requirement value of the task; or performing a weighted calculation on a calculated duration of time required to feedback a calculation result for the task, the amount of data processed for the task, and a calculation complexity of the task, so as to obtain the calculation capability requirement value of the task.

In practical applications, the image reconstruction apparatus 50 may be located on a host in an MR system.

Figure 6:
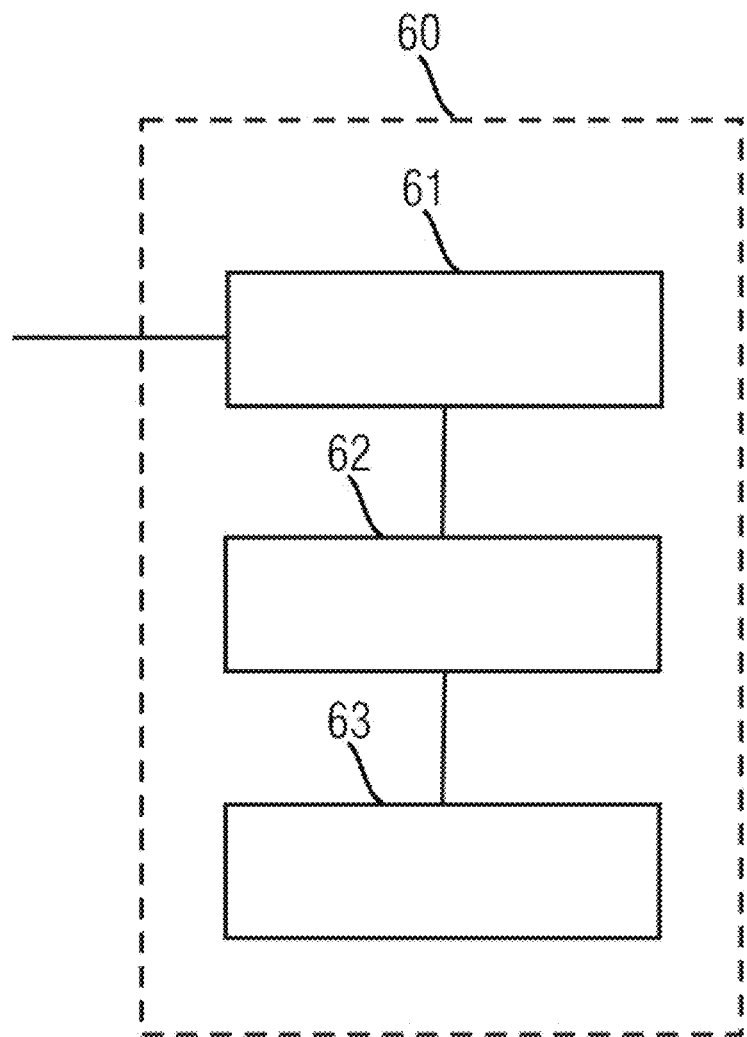
FIG. 6 is a schematic structural diagram of an image reconstruction apparatus in MRI provided in another embodiment of the present disclosure.

FIG. 6 is a schematic structural diagram of an image reconstruction apparatus 60 in MRI provided in another embodiment of the present disclosure. The apparatus 60 is located in a shared image reconstruction apparatus, and the shared image reconstruction apparatus is shared among a plurality of MR systems. The image reconstruction apparatus 60 in MRI comprises: a task priority calculation module 61, a task queue management module 62, and a task performing module 63.

The task priority calculation module 61 receives an image reconstruction task sent by an MR system, calculates the priority of the task, and sends the image reconstruction task and the priority of the task to the task queue management module 62, wherein the image reconstruction task is an image reconstruction task in image reconstruction tasks to be reconstructed generated by the MR system that has a calculation capability requirement value greater than a predetermined threshold.

The task queue management module 62 receives the image reconstruction task and the priority of the task which are sent by the task priority calculation module 61, and places the task into a task queue according to the priority of the task, wherein tasks in the task queue are arranged sequentially in descending order of priorities.

The task performing module 63 sequentially reads tasks from the task queue maintained by the task queue management module 62, and performs the read tasks.

In one optional embodiment, calculating the priority of the task by the task priority calculation module 61 comprises:
performing a weighted calculation on the calculation capability requirement value of the task and a waiting duration for the task in the task queue, so as to obtain the priority of the task, wherein the calculation capability requirement value is calculated, based on a calculated feedback duration required for the task, the amount of data processed for the task, and a calculation complexity of the task, and sent by the MR system to the task priority calculation module 61; or performing a weighted calculation on a calculated duration of time required to feedback a calculation result for the task, the amount of data processed by the task, a calculation complexity of the task, and a waiting duration for the task in the task queue so as to obtain the priority of the task, wherein the calculated feedback duration required for the task is sent by the MR system.

In one optional embodiment, the task queue management module 62 further comprises:
notifying, when a task is newly added to the task queue or a task has been performed, the task priority calculation module of recalculating the priority of each task, and adjusting the position of each task in the task queue based on a new priority of each task obtained via calculation by the task priority calculation module.

An embodiment of the present disclosure also provides an image reconstruction system in MRI, the system comprising: a plurality of MR systems and one shared image reconstruction apparatus, wherein the MR system comprises the above-mentioned image reconstruction apparatus 50 in MRI, and the shared image reconstruction apparatus comprises the above-mentioned image reconstruction apparatus 60 in MRI.

An embodiment of the present disclosure also provides a computer readable storage medium, which has a computer program stored thereon, wherein when the computer program is executed by a processor, steps of the image reconstruction method in MRI, as described in steps 101 to 104, or 201 to 204, or 301 to 309 are implemented.

Figure 7:
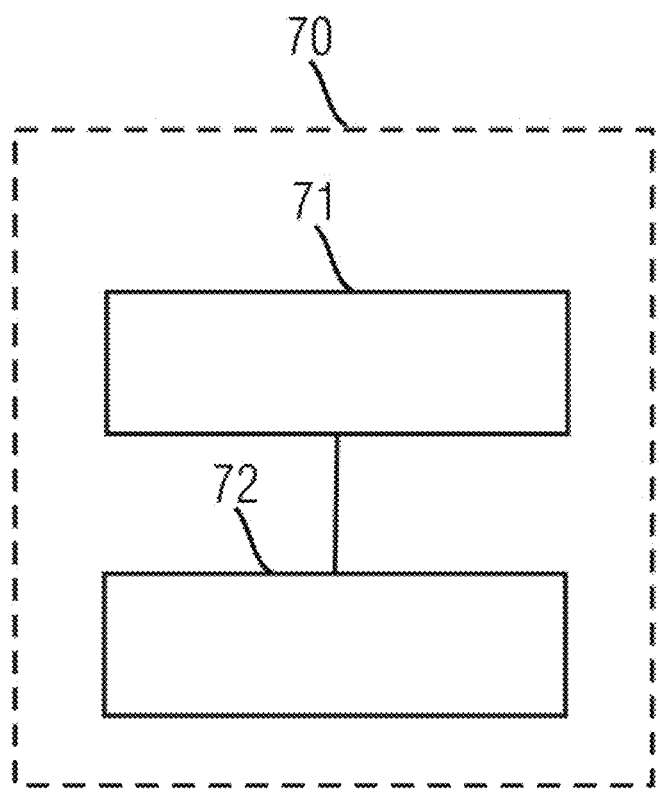
FIG. 7 is a schematic structural diagram of an image reconstruction apparatus in MRI provided in still another embodiment of the present disclosure.

FIG. 7 is a schematic structural diagram of an image reconstruction apparatus 70 in MRI provided in still another embodiment of the present disclosure. The apparatus 70 comprises: a processor 71 and a memory 72, wherein the memory 72 stores an application program executable by the processor 71 that is used to cause the processor 71 to perform the steps of the image reconstruction method in MRI, as described in steps 101 to 104, or 201 to 204, or 301 to 309. In various embodiments, the memory 72 may be implemented as any suitable type of storage medium including volatile and non-volatile storage types. As an example, the memory 72 may be implemented as a non-transitory computer-readable medium, storing one or more of the application programs as machine-readable instructions, logic, code, etc., that are executed by the processor 71 to perform the steps of the image reconstruction methods in MRI as discussed herein.

The beneficial technical effects of the embodiments of the present disclosure are as follows:
an image reconstruction task with a higher calculation performance requirement is sent to a shared image reconstruction apparatus with a higher performance for processing, while an image reconstruction task with a lower calculation performance requirement is sent to a local image reconstruction apparatus with an ordinary performance for processing, thereby reducing the number of shared image reconstruction apparatuses with a higher performance and reducing the hardware cost required for image reconstruction, and also reducing the energy consumption due to the high consumption of energy by a shared image reconstruction apparatus with a higher performance.

The foregoing description is only preferred embodiments of the present disclosure and is not intended to limit the present disclosure, and any modifications, equivalent substitutions, improvements, etc. made within the spirit and principles of the present disclosure shall be included within the scope of protection of the present disclosure.

The operation and functionality of the various embodiments described in the present disclosure may be described with respect to various "modules," such as those shown in FIGS. 5-7 for instance. These modules may operate, for example, as any suitable combination of hardware and software. For instance, the modules may include and/or access executable code, logic, machine-readable instructions, etc., that may be utilized by one or more hardware processors to perform the corresponding functions as described herein.

What is claimed is:

1. An image reconstruction method in magnetic resonance imaging, comprising:
calculating, by a magnetic resonance system for each of a plurality of image reconstruction tasks to be performed, a calculation capability requirement value;
when the calculation capability requirement value for an image reconstruction task from among the plurality of image reconstruction tasks is greater than the predetermined threshold, sending the image reconstruction task to a shared image reconstruction apparatus that is shared among a plurality of magnetic resonance systems so that the shared image reconstruction apparatus performs the image reconstruction task; and
when the calculation capability requirement value for an image reconstruction task from among the plurality of image reconstruction tasks is less than the predetermined threshold, sending the image reconstruction task to a local image reconstruction apparatus so that the local image reconstruction apparatus performs the image reconstruction task,
wherein a calculation performance of the shared image reconstruction apparatus is higher than a calculation performance of the local image reconstruction apparatus.

2. The method according to claim 1, wherein calculating the calculation capability requirement value of each of the plurality of image reconstruction tasks comprises:
performing a weighted calculation using an amount of data processed for each image reconstruction task and a calculation complexity of each image reconstruction task to obtain the calculation capability requirement value of each image reconstruction task from among the plurality of image reconstruction tasks.

3. The method according to claim 1, wherein calculating the calculation capability requirement value of each of the plurality of image reconstruction tasks comprises:
performing a weighted calculation using a calculated duration of time required to feedback a calculation result to perform the image reconstruction task, an amount of data processed for the image reconstruction task, and a calculation complexity of the image reconstruction task, so as to obtain the calculation capability requirement value of the image reconstruction task.

4. The method according to claim 2, further comprising:
prior to calculating the calculation capability requirement value of the image reconstruction task:
calculating, according to a predetermined grading standard for calculating required feedback durations, a first grade value corresponding to the calculated duration of time required to feedback a calculation result to perform the image reconstruction task, with a shorter calculated required feedback duration being indicative of a higher corresponding first grade value;
calculating, according to a predetermined grading standard for determining an amount of data, a second grade value corresponding to the amount of data processed for the image reconstruction task, with a larger amount of data being indicative of a higher corresponding second grade value; and
calculating, according to predetermined calculation complexities of different algorithms, calculation complexities of one or more algorithms used to perform the image reconstruction task, and summing the calculation complexities of the algorithms used in the image reconstruction task to obtain the calculation complexity of the image reconstruction task, with a more complex algorithm being indicative of a higher calculation complexity of an algorithm,
wherein performing the weighted calculation includes performing a weighted calculation of the first grade value, the second grade value, and the calculation complexity of the image reconstruction task.

5. The method according to claim 3, further comprising:
prior to calculating the calculation capability requirement value of the image reconstruction task:
calculating, according to a predetermined grading standard for calculating required feedback durations, a first grade corresponding to the calculated duration of time required to feedback a calculation result to perform the image reconstruction task, with a shorter calculated required feedback duration being indicative of a higher corresponding first grade value;
calculating, according to a predetermined grading standard for determining an amount of data, a second grade value corresponding to the amount of data processed for the image reconstruction task, with a larger amount of data being indicative of a higher corresponding second grade value; and
calculating, according to predetermined calculation complexities of different algorithms, calculation complexities of one or more algorithms used to perform the image reconstruction task, and summing the calculation complexities of the algorithms used in the image reconstruction task to obtain the calculation complexity of the image reconstruction task, with a more complex algorithm being indicative of a higher calculation complexity of an algorithm,
wherein performing the weighted calculation includes performing a weighted calculation of the first grade value, the second grade value, and the calculation complexity of the image reconstruction task.

6. An image reconstruction method for use in magnetic resonance imaging, comprising:
receiving, by a shared image reconstruction apparatus that is shared among a plurality of magnetic resonance systems, an image reconstruction task sent by one of the plurality of magnetic resonance systems, the image reconstruction task being one of a plurality of image reconstruction tasks generated by another one of the magnetic resonance system, the image reconstruction task having a calculation capability requirement value greater than a predetermined threshold;
calculating a priority associated with the image reconstruction task;
placing the task into a task queue according to the priority of the task, the image reconstruction tasks within the task queue being arranged sequentially in descending order of priority;
sequentially reading image reconstruction tasks from the task queue; and
performing the image reconstruction tasks read from the task queue.

7. The method according to claim 6, wherein calculating the priority of the image reconstruction task comprises:
performing a weighted calculation on the calculation capability requirement value of the image reconstruction task and a waiting duration for the image reconstruction task in the task queue to obtain the priority of the image reconstruction task,
wherein the calculation capability requirement value is calculated based on a calculated duration of time required to feedback a calculation result to perform the image reconstruction task, an amount of data processed for the image reconstruction task, and a calculation complexity of the image reconstruction task.

8. The method according to claim 6, wherein calculating the priority of the image reconstruction task comprises:

performing a weighted calculation on the calculated duration of time required to feedback a calculation result to perform the image reconstruction task, an amount of data processed for the task, a calculation complexity of the task, and a waiting duration of the image reconstruction task in the task queue to obtain the priority of the task.

9. The method according to claim 8, further comprising:
prior to performing the weighted calculation on the calculated duration of time required to feedback a calculation result to perform the image reconstruction task, the amount of data processed for the image reconstruction task, the calculation complexity of the image reconstruction task, and the waiting duration for the image reconstruction task in the task queue:
calculating, according to a predetermined grading standard for calculating required feedback durations, a first grade value corresponding to the calculated duration of time required to feedback a calculation result to perform the image reconstruction task, with a shorter calculated required feedback duration being indicative of a higher corresponding first grade value;
calculating, according to a predetermined grading standard for determining an amount of data, a second grade value corresponding to the amount of data processed for the image reconstruction task, with a larger amount of data being indicative of a higher corresponding second grade value;
calculating, according to predetermined calculation complexities of different algorithms, calculation complexities of one or more algorithms used to perform the image reconstruction task, and summing the calculation complexities of the algorithms used in the image reconstruction task to obtain the calculation complexity, with a more complex algorithm being indicative of a higher calculation complexity of an algorithm; and
calculating, according to a predetermined grading standard for waiting durations for image reconstructions tasks in a task queue, a third grade value corresponding to a waiting duration for the image reconstruction task in the task queue, with a longer waiting duration being indicative of a higher corresponding grade value,
wherein performing the weighted calculation includes performing a weighted calculation on the first grade value, the second grade value, and the third grade value corresponding to the waiting duration for the image reconstruction task in the task queue.

10. The method according to claim 6, further comprising:
recalculating, when an image reconstruction task is newly added to the task queue or a image reconstruction task has been performed, the priority of each task from among the plurality of image reconstruction tasks, and adjusting a position of each of the plurality of image reconstruction tasks in the task queue based on a recalculation.

11. An image reconstruction apparatus for use in magnetic resonance imaging, the image reconstruction apparatus being part of a magnetic resonance system, the apparatus comprising:
a calculation capability requirement value calculation module configured to calculate, for each of a plurality of image reconstruction tasks to be performed, a calculation capability requirement value; and a task distribution module configured to (i) when the calculation capability requirement value for a image reconstruction task from among the plurality of image reconstruction tasks is greater than the predetermined threshold send the image reconstruction task to a shared image reconstruction apparatus that is shared among a plurality of magnetic resonance systems so that the shared image reconstruction apparatus performs the image reconstruction task, and (ii) when the calculation capability requirement value for an image reconstruction task from among the plurality of image reconstruction tasks is less than the predetermined threshold, send the image reconstruction task to a local image reconstruction apparatus so that the local image reconstruction apparatus performs the image reconstruction task, wherein a calculation performance of the shared image reconstruction apparatus is higher than a calculation performance of the local image reconstruction apparatus.

12. The apparatus according to claim 11, wherein the calculation capability requirement value calculation module is configured to calculate the calculation capability requirement value of the image reconstruction task by performing a weighted calculation using an amount of data processed for each image reconstruction task and a calculation complexity of each image reconstruction task to obtain the calculation capability requirement value of each image reconstruction task from among the plurality of image reconstruction tasks.

13. The apparatus according to claim 11, wherein the calculation capability requirement value calculation module is configured to calculate the calculation capability requirement value of the image reconstruction task by performing a weighted calculation using a calculated duration of time required to feedback a calculation result to perform the image reconstruction task, an amount of data processed for the image reconstruction task, and a calculation complexity of the image reconstruction task, so as to obtain the calculation capability requirement value of the image reconstruction task.

14. An image reconstruction apparatus for use in magnetic resonance imaging, the image reconstruction apparatus being part of a shared image reconstruction apparatus that is shared among a plurality of magnetic resonance systems, the image reconstruction apparatus comprising:

a task priority calculation module configured to receive an image reconstruction task sent by a magnetic resonance system, and to calculate a priority of the image reconstruction task, the image reconstruction task being one of a plurality of image reconstruction tasks generated by another one of the magnetic resonance system, the image reconstruction task having a calculation capability requirement value greater than a predetermined threshold;

a task queue management module configured to place the image reconstruction task into a task queue according to the priority of the image reconstruction task, the image reconstruction tasks within the task queue being arranged sequentially in descending order of priority; and a task performing module configured to sequentially read image reconstruction tasks from the task queue and to perform the read image reconstruction tasks.

15. The image reconstruction apparatus according to claim 14, wherein the task priority calculation module is configured to perform a weighted calculation on the calculation capability requirement value of the image reconstruction task and a waiting duration for the image reconstruction task in the task queue to obtain the priority of the image reconstruction task, wherein the calculation capability requirement value is calculated based on a calculated duration of time required to feedback a calculation result perform the image reconstruction task, an amount of data processed for the image reconstruction task, and a calculation complexity of the image reconstruction task.

16. The image reconstruction apparatus according to claim 14, wherein the task priority calculation module is configured to perform a weighted calculation on the calculated duration of time required to feedback a calculation result to perform the image reconstruction task, an amount of data processed for the task, a calculation complexity of the task, and a waiting duration of the image reconstruction task in the task queue to obtain the priority of the task.

17. The image reconstruction apparatus according to claim 16, the task priority calculation module is configured to, prior to performing the weighted calculation on the calculated duration of time required to feedback a calculation result to perform the image reconstruction task, the amount of data processed for the image reconstruction task, the calculation complexity of the image reconstruction task, and the waiting duration for the image reconstruction task in the task queue:

calculate, according to a predetermined grading standard for calculating required feedback durations, a first grade value corresponding to the calculated duration of time required to feedback a calculation result ty perform the image reconstruction task, with a shorter calculated required feedback duration being indicative of a higher corresponding first grade value;

calculate, according to a predetermined grading standard for determining an amount of data, a second grade value corresponding to the amount of data processed for the image reconstruction task, with a larger amount of data being indicative of a higher corresponding second grade value;

calculate, according to predetermined calculation complexities of different algorithms, calculation complexities of one or more algorithms used to perform the image reconstruction task, and summing the calculation complexities of the algorithms used in the image reconstruction task to obtain the calculation complexity, with a more complex algorithm being indicative of a higher calculation complexity of an algorithm; and calculate, according to a predetermined grading standard for waiting durations for image reconstructions tasks in a task queue, a third grade value corresponding to a waiting duration for the image reconstruction task in the task queue, with a longer waiting duration being indicative of a higher corresponding grade value, wherein performing the weighted calculation includes performing a weighted calculation on the first grade value, the second grade value, and the third grade value corresponding to the waiting duration for the image reconstruction task in the task queue.

18. The image reconstruction apparatus according to claim 14, wherein the task priority calculation module is configured to recalculate, when an image reconstruction task is newly added to the task queue or an image reconstruction task has been performed, the priority of each image reconstruction task from among the plurality of image reconstruction tasks, and to adjust a position of each of the plurality of image reconstruction tasks in the task queue based on the recalculation.

19. The image reconstruction apparatus according to claim 18, wherein the task queue management module is further configured to generate a notification when an image reconstruction task is newly added to the task queue or an image reconstruction task has been performed.

* * * * *